United States Patent [19]

Kremer

[11] Patent Number: 4,843,921
[45] Date of Patent: Jul. 4, 1989

[54] TWISTED CORD ACTUATOR

[76] Inventor: Stephen R. Kremer, 3283 Yelton La., Amelia, Ohio 45102

[21] Appl. No.: 182,880

[22] Filed: Apr. 18, 1988

[51] Int. Cl.$^4$ ............................................ F16H 27/02
[52] U.S. Cl. ........................................ 64/89.2; 901/21; 901/36
[58] Field of Search ...................... 74/89.2; 901/21, 36

[56]   References Cited
       U.S. PATENT DOCUMENTS

| 2,027,386 | 1/1936 | Krümer | 74/99 |
| 3,864,983 | 2/1975 | Jacobsen | 74/89 |
| 4,203,329 | 5/1980 | Lopez | 74/89.2 |
| 4,246,661 | 1/1981 | Pinson | 3/1.1 |
| 4,272,997 | 6/1981 | Groth | 74/89.22 |
| 4,534,232 | 8/1985 | Stieg | 74/89.2 |
| 4,593,571 | 6/1986 | Schwarz | 74/162 |
| 4,597,308 | 7/1986 | Tanaka et al. | 74/866 |
| 4,654,736 | 3/1987 | Kaczeus | 360/106 |
| 4,765,795 | 8/1988 | Rebman | 901/21 |

OTHER PUBLICATIONS

Salisbury-Articulated Hands-Spring 1982-J' Robotic Research, pp. 4 & 5.
Salisbury-Articulated Hand-Jul. 1984-1st Int'al Symposium-, p. 156 & 157.
Jacobsen-Utah/M.I.T.' Hand-Aug. 1984-Journal of Robotic's Research, pp. 24 & 26.
Nakano-Hitachi's Robotic Hand-Jul. 1984-Robotic's Age, pp. 18, 19 & 20.

Primary Examiner—Leslie A. Braun
Assistant Examiner—Scott Anchell

[57]   ABSTRACT

This invention relates particularly to a drive mechanism for converting rotary to unidirectional linear movement for use in actuation of hinged members of robotic, prosthetic, and other like devices. The twisted cord actuator includes a motor with an axial shaft to which, by a coupling, the single free end of two or more cords are attached. The opposing ends of the cords are attached to the moveable member. As the shaft rotates the cords are twisted around each other in helical fashion. Thus their combined length is shortened. In this invention the rotating device represents the muscle and the twisting of the cords, the tendons. The twisting pair of cords may then be threaded through a sheath to act as a pull cable for use as a tendon for an artifical finger or robotic arm. The values of this invention are low cost, ease of use and variability of design. In most applications the present invention may be matched to the load by the careful selection of the motor, cord diameter, and cord length without the use of a gear reducer. This combination creates a low inertia resilient actuator.

8 Claims, 2 Drawing Sheets

TWISTED CORD ACTUATOR

FIELD OF THE INVENTION

This invention relates particularly to a drive mechanism for converting rotary to unidirectional linear movement for use in actuation of hinged members of robotic, prosthetic, and other like devices.

BACKGROUND OF THE INVENTION

To date there are several types of rotational to linear converters in common use. Systems such as the conventional lead screw, drum and cable, and hydraulic or pneumatic cylinders are in common use in robotic and prosthetic devices. All the research into the design of artificial hands or grippers have used one of these methods, for example: MIT Hand, Salisbury Hand, and the Hitachi gripper. The complexity and consequently the cost of these drive mechanisms has not been lowered to match the sensory and computing power advances made in the field of robotics.

The object of the present invention is to provide an actuating mechanism which closely performs and maintains the same physical function and configuration as a muscle and tendon.

Another object is to show the ease of use of the present invention in a closed-loop system and to make obvious it lowers the cost of achieving controlled translational movement.

In the present invention the force is high when motion is small and the force increases as motion decreases. This is a valuable feature when being matched to hinged member designs where the force and motion are not the same for different positions in the moving member's swing. Methods are shown by which the invention's mechanical gain may be changed during actuating length. It is obvious if opposing ends of a rotating shaft are used then bidirectional actuation may be attained.

Briefly described, the twisted cord actuator includes a motor with an axial shaft to which, by a coupling, the single free end of two or more cords are attached. The opposing ends of the cords are attached to the moveable member. As the shaft rotates the cords are twisted around each other in helical fashion. Thus their combined length is shortened.

In this invention the rotating device represents the muscle and the twisting of the cords, the tendons. The twisting pair of cords may then be threaded through a sheath to act as a pull cable. For example, for use as a tendon for an artificial finger or robotic arm. The values of this invention are low cost, ease of use and variability of design. In most applications the present invention may be matched to the load by the careful selection of the motor, cord diameter, and cord length without the use of a gear reducer. This combination creates a low inertia resilient actuator.

DETAILED DESCRIPTION

Figure 1:
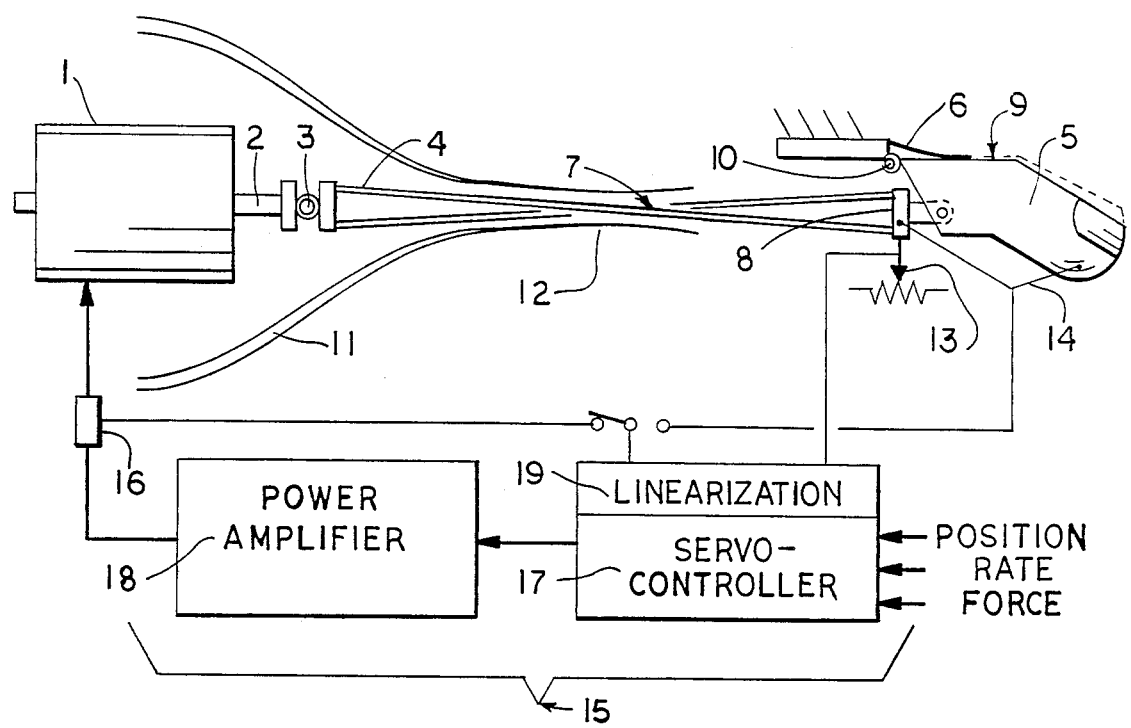
FIG. 1 is an illustration of an actuating mechanism embodying features of one form of the invention used to actuate a robotic finger.

Referring to the detailed description of the invention, the embodiment of FIG. 1 includes a motor 1 of the type that has a rotating output shaft 2. For example, the motor 1 could be a ⅛ horsepower, low inertia armature, direct current motor. To the shaft 2 a coupling 3 is used to connect the free end of each of two or more cords 4. The cords could be of a nonmetallic type allowing for resilience, duty cycle, and efficiency as required by the application. By way of example, the application could use two braided nylon cords. The opposing free end of each of the cords 4 is connected to the hinged member 5 by laying them parallel to each other and on the same line as the axis of the rotating output shaft 2. Being coaxial is not critical and could be accommodated for by using a universal joint or a flexible joint in the coupling 3 means. The opposing ends of the cords 4 are joined and pinned by a clevis 8 to a hinged member 5 not allowing the cords 4 at the clevis to rotate about their mean axis. The cords 4 laying next to each other are held taut by the spring 6 or the load. Rotation of the shaft 2 will cause the cords to twist around each other in helical fashion. As twisting continues the cords 4 shorten in length by becoming a helical bundle 7. At the start of actuation the cords 4 are not twisted around each other; as the cords start to twist, the motion at the clevis 8 is small but the force is high. As the rotation of the shaft continues, the rate of motion at the clevis end increases and the force decreases. This nonlinearity of force and motion is a valuable feature when matched with a hinged member design 9 which is actuated at a distance from the hinged point 10. By proper selection of motor, cord diameter, and cord length the hinged member's dynamics may be tailored to perform the desired function. This combination creates a low inertia and resilient actuator.

The twisting of cords may be used to actuate other differently supported members than hinged. For example, the use as a drive mechanism in an X-ray Bucky, which requires a repetitive pull in a straight line.

The present invention when used as a muscle 11 and tendon 12, as shown in FIG. 1, has a motion and force which is not linearly related to the shaft 2 angular velocity. In many applications closed-loop control 15 would be required. As shown in FIG. 1, the actuator can use a classical means of control by using a sensor 13 to determine true position and velocity at the hinged member 5 or load. Force at the clevis 8 or in the actuated member can be determined by use of a strain or force sensor 14. A less direct method of determining force, but cost effective, is to use a sensor 16 to monitor motor current. These feedback elements would need linearization circuitry 19 depending on location and type of feedback used. The reference inputs for position, rate, and force are then set by a voltage or current into the summing amplifier of the servo-controller 17. The power amplifier 18 supplies proportional power to the motor as dictated by the controller.

Figure 2:
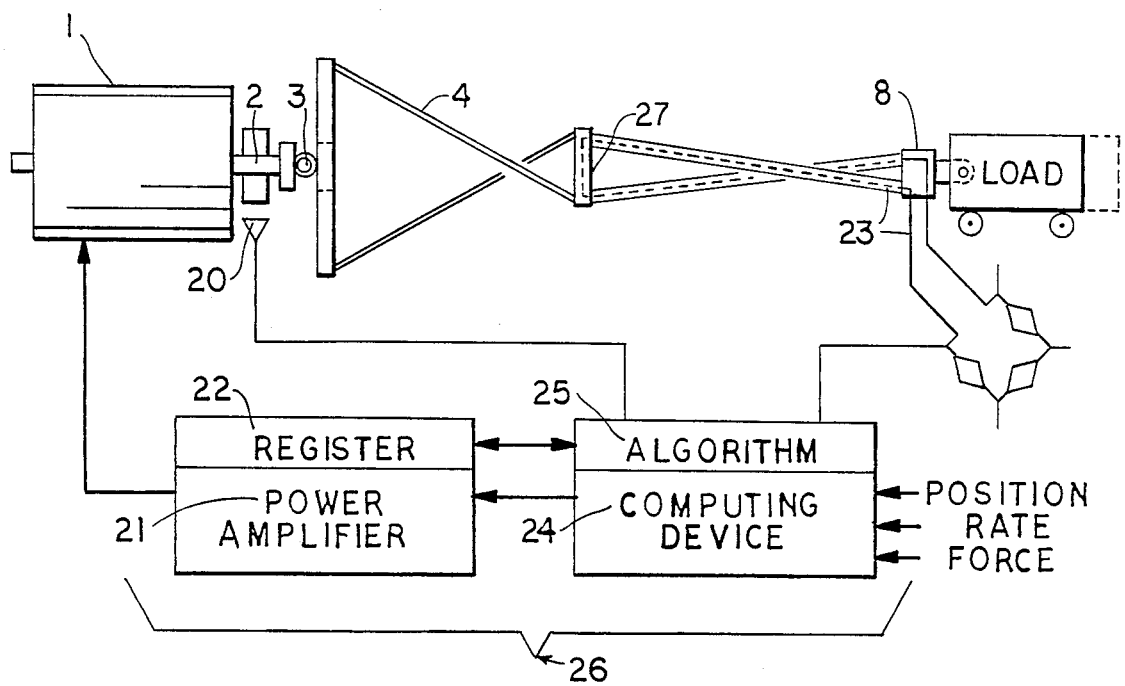
FIG. 2 illustrates a second means of control and one method to contour mechanical gain.

Referring to FIG. 2 is an actuator embodying a second form of control means. This method uses open-loop control 26 of position, rate, and velocity of the number or load. In this invention the motor 1 is the type in which the shaft 2 has a known incremental angular rotation either by use of sensor 20 or by incremental angular rotation of the shaft by pulsed steps from the power amplifier 21. The total count of pulses is stored in a register 22 for use by computing device 24. By way of example, a method that uses a stepping motor whose step rate and step count are calculated by use of an algorithm that defines the dynamics of the system. Force at the actuating end can be measured by conventional strain sensor or designed into the cords. The cords are constructed with the addition of a resistance wire 23. The resistance wire 23 is used as one leg of a resistance bridge thus providing feedback for force. To linearize the feedback elements the computing device 24 uses circuitry, a look-up table, or an algorithm 25. The computing device 24 provides the step rate and number of steps to the power amplifier 21 as needed. The advantages of the present invention over lead screw or drum and cable actuators are ease of application and the many possible variations. The invention of FIG. 2 could use cords 4 of different materials and length to effect mechanical gain and elasticity. Another way to effect the mechanical gain contour is to separate the cords 4 at the coupler 3 or the clevis 8 or add a spacer 27 some distance between coupler and clevis 8.

Figure 3:
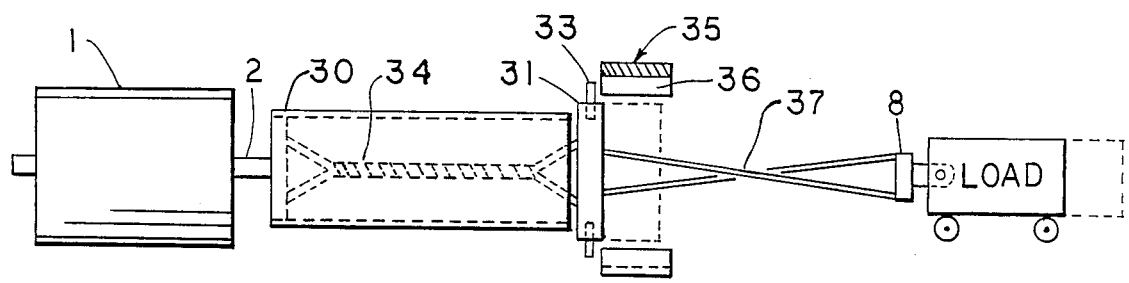
FIG. 3 is a plane view of one variation of the invention providing sequencial motion of different mechanical gains.

Referring to FIG. 3, is a form of the actuator in which a fraction of the total length is selected to change intermittently or in sequencial fashion. In the present invention the cords 34 actuate prior to cords 37. The cords 34 are placed internal to a rigid tube 30 with one end of each cord coupled to the shaft 2. The opposite ends of the cords 34 are connected to a solid disk 31 that is larger than the diameter of the rigid tube 30. To insure that the cords internal to the tube are the first to twist, the solid disk 31 has a protruding pin 33 which is blocked by an external catch mechanism 35. The catch mechanism prevents rotation of disk 31 and thus the twisting of cords 37. As the shaft 2 rotates the cords 34 internal to the rigid tube 30 shorten. As input shaft rotation continues, the pin 33 leaves the grooved guideway of block 36. The solid disk 31 is then allowed to rotate. In this position the disk 31 is tight against the end of the rigid tube 30. All the shaft rotation is then transferred by the rigid tube to the next section of cords 37 of a different mechanical gain. This assembly could be designed to have multiple sections of various gains.

Figure 4:
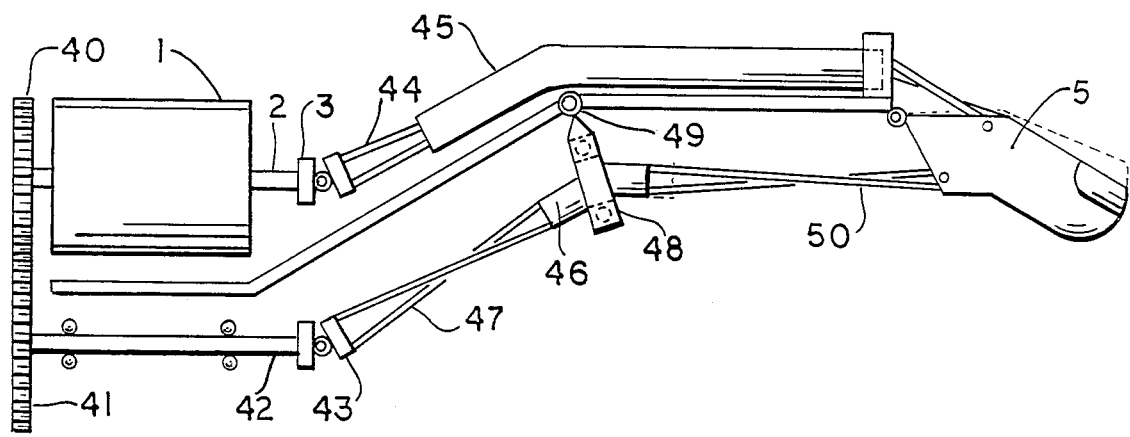
FIG. 4 is a view of two forms of the invention combined to provide movement of a robotic finger separated by a flexible joint.

FIG. 4 shows a double acting form of the actuator used to transfer motion and force around a corner or hinged joint 49. Both ends of the motor shaft 2 are used. The gears 40 and 41 are sized for proper mechanical gain. The angular rotation of motor shaft 2 is imparted to coupling 3 to which the free ends of a pair of cords 44 are attached. The opposing ends of cords 44 are threaded through a flexible sheath 45 and attached to the hinged member 5 so as not to rotate at the point of attachment. As shaft 2 rotates the attached cords 44 perform the function of a pull cable. FIG. 4 shows a second means of actuation able to transfer both linear motion and angular rotation at an oblique angle past the hinged joint 49. This method uses a flexible coupling 46. The flexible coupling has a length greater than the possible change in length of the first bundle of cords 47. The first bundle of cords 47 are attached to gear shaft 42 by coupling 43. The shortening and rotation of the cords 47 are transferred to the flexible coupling 46. Support is provided to the flexible coupling by a bearing 48 mounted near the pivot point of the joint 49. The flexible coupling 46 is made of a material which allows it to slide on the inside surface of the bearing 48. Rotational and linear motion may then be imparted to a second set of cords 50 of a different mechanical gain.

The embodiments described herein are at present preferred. It is understood that various modifications and improvements may be made once this invention becomes popularized.

I claim:

1. A drive mechanism for converting rotary motion to intermittent unidirectional motion for use as a cost effective actuator upon a load, comprising:
   (a) a plurality of longitudinally strung cords of substantially equal length,
   (b) a coupling means secured to a first end of each of said cords,
   (c) a rotating shaft secured to said coupling means and being driven by a motor.
   (d) a second end of each of said cords being secured to said load and being fixed relative to each other,
   (e) means controlling the motor to regulate the position of the load, the velocity of the load, the acceleration of the load, and/or the force upon the load,
   (f) whereby the controlling of the motor causes the rotating shaft to impart an intertwining of the cords around each other in helical fashion bringing the first and second ends of the cords towards and away from each other.

2. The drive mechanism of claim 1 further characterized by and including: (a) a means for tailoring mechanical characteristics of said cords by separation at the cord ends or by use of a spacer along their length.

3. The drive mechanism of claim 1 further characterized by and including: (a) a means for setting intermittent mechanical characteristics by use of a mechanism to select a section of the total length of the cords for actuation.

4. The drive mechanism of claim 1 further characterized by and including: (a) a sheath means for flexibly surrounding the cords.

5. The drive mechanism of claim 1 further characterized by and including: (a) a second coupling means to provide for actuation around a hinged joint by use of a flexible coupling supported by a bearing which transfers longitudinal and rotational motion.

6. The drive mechanism of claim 1 further characterized by and including: (a) a sensing means as part of the cord construction by use of a resistance wire to monitor for a broken cord or cord strain.

7. The drive mechanism of claim 1 further characterized by and including: (a) said means controlling includes a closed-loop servo-controller and a sensor.

8. The drive mechanism of claim 1 further characterized by and including: (a) said means controlling includes a computing device having an algorithm or a look-up table.

* * * * *